United States Patent [19]

Kostinko

[11] 4,235,856
[45] Nov. 25, 1980

[54] METHOD OF PRODUCING A ZEOLITE OF CONTROLLED PARTICLE SIZE

[75] Inventor: John A. Kostinko, Bel Air, Md.

[73] Assignee: J. M. Huber Corporation, Locust, N.J.

[21] Appl. No.: 971,584

[22] Filed: Dec. 20, 1978

[51] Int. Cl.³ ............................................. C01B 33/28
[52] U.S. Cl. ..................................... 423/329; 423/328
[58] Field of Search ............................. 423/328–330; 252/455 Z

[56] References Cited

U.S. PATENT DOCUMENTS

| | | | |
|---|---|---|---|
| 2,882,243 | 4/1959 | Milton | 423/328 |
| 2,882,244 | 4/1959 | Milton | 423/328 |
| 2,982,612 | 5/1961 | Barrer et al. | 423/329 |
| 3,058,805 | 10/1962 | Weber | 423/328 |
| 4,041,135 | 8/1977 | Williams et al. | 423/329 |

Primary Examiner—Edward J. Meros
Attorney, Agent, or Firm—Ernest A. Schaal; Robert L. Price; Harold H. Flanders

[57] ABSTRACT

Zeolite X can be produced in a reaction mixture having a $SiO_2/Al_2O_3$ molar ratio greater than 5:1. Zeolite A can be produced in a reaction mixture having a $SiO_2/Al_2O_3$ molar ratio greater than 3:1. The resulting zeolite X and zeolite A have an average particle size below 2 microns. A combination of zeolite X and zeolite A can be made in the same reaction. Sand can be used as a source of silica in the production of zeolite Y by activating the sand with from 50 to 2000 ppm alumina.

5 Claims, 5 Drawing Figures

ZEOLITE X

ZEOLITE A

ZEOLITES X AND A

ZEOLITE Y

CALCIUM CARBONATE DEPLETION RATE

METHOD OF PRODUCING A ZEOLITE OF CONTROLLED PARTICLE SIZE

BACKGROUND OF THE INVENTION

1. Field of the Invention

In general, the present invention relates to the production of zeolites.

2. Description of the Prior Art

Certain naturally occurring hydrated metal aluminum silicates are called zeolites. The synthetic adsorbents of the invention have compositions similar to some of the natural zeolites. The most common of these zeolites are sodium zeolites.

Certain adsorbents, including zeolites A, X and Y, selectively adsorb molecules on the basis of the size and shape of the adsorbate molecule and are called molecular sieves. Molecular sieves have a sorption area available on the inside of a large number of uniformly sized pores of molecular dimensions. With such an arrangement, molecules of a certain size and shape enter ahe pores and are adsorbed while larger or differently shaped molecules are excluded. Not all adsorbents behave in the manner of molecular sieves. The common adsorbents, charcoal and silica gel, for example, do not exhibit molecular sieve action.

Zeolites consist bascially of a three-dimensional framework of $SiO_4$ and $AlO_4$ tetrahedra. The tetrahedra are crosslinked by the sharing of oxygen atoms so that the ratio of oxygen atoms to the total of the aluminum and silicon atoms is equal to two or $O/(Al+Si)=2$. The electrovalence of each tetrahedra containing aluminum is balanced by the inclusion in the crystal of a cation, for example a sodium ion. This balance may be expressed by the formula $Al_2/Na_2=1$. The spaces between the tetrahedra are occupied by water molecules prior to dehydration.

Zeolites may be activated by heating to effect the loss of the water of hydration. The dehydration results in crystals interlaced with channels of molecular dimensions that offer very high surface areas for the adsorption of foreign molecules. The interstitial channels of zeolite X are of a size such that heptacosafluorotributylamine and larger molecules will not enter into the channels. The interstitial channels of zeolite A will not accept molecules larger than 5.5 Å.

Factors influencing occlusion by activated zeolite crystals are the size and polarizing power of the interstitial cation, the polarizability and polarity of the occluded molecules, the dimensions and shape of the sorbed molecule relative to those of the channels, the duration and severity of dehydration and desorption, and the presence of foreign molecules in the interstitial channels. It will be understood that the refusal characteristics of zeolites are quite as important as the adsorptive or positive adsorption characteristics. For instance, if benzene and heptacosafluorotributylamine $(C_4F_9)_3N$ are to be separated, it is as essential that the crystals refuse the heptacosafluorotributylamine as it is that they adsorb the benzene. If water and another material are to be separated, it is essential that the crystals refuse the other material as it is that they absorb the water.

Zeolites A, X and Y may be distinguished from other zeolite and silicates on the basis of their x-ray powder diffraction patterns and certain physical characteristics. The x-ray patterns for several of these zeolites are described below. The composition and density are among the characteristics which have been found to be important in identifying these zeolites.

The basic formula for all crystalline sodium zeolites may be represented as follows:

$$Na_2O:Al_2O_3:XSiO_2:yH_2O$$

In general, a particular crystalline zeolite will have values for x and y that fall in a definite range. The value x for a particular zeolite will vary somewhat since the aluminum atoms and the silicon atoms occupy essentially equivalent positions in the lattice. Minor variations in the relative numbers of these atoms does not significantly alter the crystal structure of physical properties of the zeolite. For zeolite X, an average value for x is about 2.5 with the x value falling within the range $2.5\pm0.5$. For zeolite A, the x value falls within the range $1.85\pm0.5$.

The value of y is not necessarily an invariant for all samples of zeolites. This is true because various exchangeable ions are of different size, and, since there is no major change in the crystal lattice dimensions upon ion exchange, the space available in the pores of the zeolite to accommodate water molecules varies.

The average value for y determined for zeolite X is 6.2. For zeolite A it is 5.1.

In zeolites synthesized according to the preferred procedure, the ratio $Na_2O/Al_2O_3$ should equal one. But if all the excess sodium present in the mother liquor is not washed out of the precipitated product, analysis may show a ratio greater than one, and if the washing is carried too far, some sodium may be ion exchanged by hydrogen, and the ratio will drop below one. It has been found that due to the ease with which hydrogen exchange takes place, the ratio for zeolite X lies in the range of $$\frac{Na_2O}{Al_2O_3} = 0.9 \pm 0.2$$

The ratio for zeolite A lies in the range of $$\frac{Na_2O}{Al_2O_3} = 1.0 \pm 0.2$$

Thus the formula for zeolite A may be written as follows:

$$1.0\pm0.2\ Na_2O:Al_2O_3:\ 1.85\pm0.5\ SiO_2:yH_2O$$

The formula for zeolite X may be written as follows:

$$0.9\pm0.2\ Na_2O:Al_2O_3:2.5\pm0.5\ SiO_2:yH_2O$$

The formula for zeolite Y may be written as follows:

$$0.9\pm0.2\ Na_2O:Al_2O_3:4.5\pm1.5\ SiO_2:yH_2O$$

"y" may be any value up to 6 for zeolite A; any value up to 8 for zeolite X; and any value up to 9 for zeolite Y.

The pores of zeolites normally contain water.

The above formulas represent the chemical analysis of zeolites A, X and Y. When other materials as well as water are in the pores, chemical analysis will show a lower value of y and the presence of other adsorbates. The presence in the crystal lattice of materials volatile at temperatures below about 600° C. does not significantly alter the usefulness of the zeolites as an adsorbent since the pores are usually freed of such volatile materials during activation.

Among the ways of identifying zeolites and distinguishing them from other zeolites and other crystalline substances, the x-ray power diffraction pattern has been found to be a useful tool. In obtaining the x-ray powder diffraction patterns, standard techniques were employed. The radiation was the $K\alpha$ doublet of copper, and a Geiger counter spectrometer with a strip chart pen recorder was used. The peak heights, I, and the positions as a function of $2\theta$ where $\theta$ is the Bragg angle, were read from the spectrometer chart. From these, the relative intensities, $$100 \text{ I}/\text{I}_o$$

where $I_o$ is the intensity of the strongest line or peak, and d the interplanar spacing in Å corresponding to the recorded lines were calculated.

X-ray powder diffraction data for sodium zeolite X are given in Tabble A. $100 \text{ I}/\text{I}_o$ and the d values in angstroms (Å) for the observed lines for zeolite X are also given. The x-ray patterns indicate a cubic unit cell of dimensions between 24.5 Å and 25.5 Å. In a separate column are listed the sum of the squares of the Miller indices $(h^2+k^2+l^2)$ for a cubic unit cell that corresponds to the observed lines in the x-ray diffraction patterns. The $a_o$ value for zeolite X is 24.99 Å, where $a_o$ is the unit cell edge.

TABLE A

X-RAY DIFFRACTION PATTERN FOR ZEOLITE X

| $h^2 + k^2 + l^2$ | $\frac{100 \text{ I}}{\text{I}_o}$ | d (Å) |
|---|---|---|
| 3 | 100 | 14.47 |
| 8 | 18 | 8.85 |
| 11 | 12 | 7.54 |
| 19 | 18 | 5.73 |
| 27 | 5 | 4.81 |
| 32 | 9 | 4.42 |
| 35 | 1 | 4.23 |
| 40 | 4 | 3.946 |
| 43 | 21 | 3.808 |
| 44 | 3 | 3.765 |
| 48 | 1 | 3.609 |
| 51 | 1 | 3.500 |
| 56 | 18 | 3.338 |
| 59 | 1 | 3.253 |
| 67 | 4 | 3.051 |
| 72 | 9 | 2.944 |
| 75 | 19 | 2.885 |
| 80 | 8 | 2.794 |
| 83 | 2 | 2.743 |
| 88 | 8 | 2.663 |
| 91 | 3 | 2.620 |
| 96 | 1 | 2.550 |
| 104 | — | — |
| 108 | 5 | 2.404 |
| 123 | 1 | 2.254 |
| 128 | 3 | 2.209 |
| 131 | 3 | 2.182 |
| 136 | 2 | 2.141 |
| 139 | 2 | 2.120 |
| 144 | 1 | 2.083 |
| 147 | — | — |
| 155 | — | — |
| 164 | 1 | 1.952 |
| 168 | 1 | 1.928 |
| 179 | — | — |
| 184 | 1 | 1.842 |
| 187 | — | — |
| 195 | 1 | 1.789 |
| 200 | 2 | 1.767 |
| 211 | 3 | 1.721 |
| 236 | — | — |

TABLE A-continued

X-RAY DIFFRACTION PATTERN FOR ZEOLITE X

| $h^2 + k^2 + l^2$ | $\frac{100 \text{ I}}{\text{I}_o}$ | d (Å) |
|---|---|---|
| 243 | 3 | 1.603 |

The more significant d values for zeolite X are given in Table B.

TABLE B

MOST SIGNIFICANT d VALUES FOR ZEOLITE X

| d Value of Reflection in A |
|---|
| 14.42 ± 0.2 |
| 8.82 ± 0.1 |
| 4.41 ± 0.05 |
| 3.80 ± 0.05 |
| 3.33 ± 0.05 |
| 2.88 ± 0.05 |
| 2.79 ± 0.05 |
| 2.66 ± 0.05 |

X-ray powder diffraction data for sodium zeolite A are given in Table C.

TABLE C

X-RAY DIFFRACTION PATTERN FOR ZEOLITE A

| $h^2 + k^2 + l^2$ | d(Å) | $\frac{100 \text{ I}}{\text{I}_o}$ |
|---|---|---|
| 1 | 12.29 | 100 |
| 2 | 8.71 | 69 |
| 3 | 7.11 | 35 |
| 4 | — | — |
| 5 | 5.51 | 25 |
| 6 | 5.03 | 2 |
| 8 | 4.36 | 6 |
| 9 | 4.107 | 36 |
| 10 | — | — |
| 11 | 3.714 | 53 |
| 12 | — | — |
| 13 | 3.417 | 16 |
| 14 | 3.293 | 47 |
| 16 | — | — |
| 17 | 2.987 | 55 |
| 18 | 2.904 | 9 |
| 20 | 2.754 | 12 |
| 21 | 2.688 | 4 |
| 22 | 2.626 | 22 |
| 24 | 2.515 | 5 |
| 25 | 2.464 | 4 |
| 26 | — | — |
| 27 | 2.371 | 3 |
| 29 | 2.289 | 1 |
| 30 | 2.249 | 3 |
| 32 | 2.177 | 7 |
| 33 | 2.144 | 10 |
| 34 | 2.113 | 3 |
| 35 | 2.083 | 4 |
| 36 | 2.053 | 9 |
| 37 | — | — |
| 38 | — | — |
| 41 | 1.924 | 7 |
| 42 | 1.901 | 4 |
| 44 | 1.858 | 2 |
| 45 | 1.837 | 3 |
| 49 | 1.759 | 2 |
| 50 | 1.743 | 13 |
| 51 | — | — |
| 53 | 1.692 | 6 |
| 54 | 1.676 | 2 |
| 57 | 1.632 | 4 |
| 59 | 1.604 | 6 |
| 61 | 1.577 | 4 |
| 62 | — | — |
| 65 | 1.528 | 2 |
| 66 | 1.516 | 1 |
| 67 | — | — |
| 68 | — | — |
| 69 | 1.483 | 3 |

TABLE C-continued

X-RAY DIFFRACTION PATTERN FOR ZEOLITE A

| $h^2 + k^2 + l^2$ | d(Å) | $\frac{100\, I}{I_o}$ |
|---|---|---|
| 70 | 1.473 | 2 |
| 72 | — | — |
| 74 | 1.432 | 3 |
| 75 | 1.422 | 2 |
| 77 | 1.404 | 5 |
| 81 | 1.369 | 2 |
| 82 | 1.360 | 8 |
| $a_o$ | 12.32 ± 0.02 | |

The more significant d values for zeolite A are given in Table D.

TABLE D

| d VALUE OF REFLECTION IN Å |
|---|
| 12.2 ± 0.2 |
| 8.6 ± 0.2 |
| 7.05 ± 0.15 |
| 4.07 ± 0.08 |
| 3.68 ± 0.07 |
| 3.38 ± 0.06 |
| 3.26 ± 0.05 |
| 2.96 ± 0.05 |
| 2.73 ± 0.05 |
| 2.60 ± 0.05 |

Zeolite Y has a characteristic x-ray powder diffraction pattern which may be employed to identify zeolite Y. The x-ray powder diffraction data are shown in Table E. The values for the interplanar spacing d, are expressed in angstrom units. The relative intensities of the lines of the x-ray powder diffraction pattern are expressed as VS (very strong), S (strong), M (medium), W (weak), and VW (very weak).

TABLE E

X-RAY DIFFRACTION PATTERN FOR ZEOLITE Y

| hkl | $h^2 + k^2 + l^2$ | d,Å | Relative Intensity |
|---|---|---|---|
| 111 | 3 | 14.37–14.15 | VS |
| 220 | 8 | 8.80–8.67 | M |
| 311 | 11 | 7.50–7.39 | M |
| 331 | 19 | 5.71–5.62 | S |
| 333,511 | 27 | 4.79–4.72 | M |
| 440 | 32 | 4.46–4.33 | M |
| 531 | 35 | 4.29–4.16 | W |
| 600,442 | 36 | 4.13–4.09 | W |
| 620 | 40 | 3.93–3.88 | W |
| 533 | 43 | 3.79–3.74 | S |
| 631 | 46 | 3.66–3.62 | M |
| 711,551 | 51 | 3.48–3.43 | VW |
| 642 | 56 | 3.33–3.28 | S |
| 733 | 67 | 3.04–3.00 | M |
| 822,660 | 72 | 2.93–2.89 | M |
| 751,555 | 75 | 2.87–2.83 | S |
| 840 | 80 | 2.78–2.74 | M |
| 911,753 | 83 | 2.73–2.69 | W |
| 664 | 88 | 2.65–2.61 | M |
| 844 | 96 | 2.54–2.50 | VW |
| 10,0,0;860 | 100 | 2.49–2.45 | VW |
| 10,2,0;862 | 104 | 2.44–2.40 | VW |
| 10,2,2;665 | 108 | 2.39–2.36 | M |
| 10,4,0;864 | 116 | 2.29–2.25 | VW |
| 11,1,1;775 | 123 | 2.24–2.21 | VW |
| 880 | 128 | 2.20–2.17 | W |
| 11,3,1;971;955 | 131 | 2.18–2.14 | VW |
| 11,3,3;973 | 139 | 2.10–2.08 | W |
| 12,0,0;884 | 144 | 2.07–2.04 | VW |
| 11,5,2;10,7,1;10,5,5 | 150 | 2.03–2.00 | VW |
| 10,8,2 | 168,171 | 1.92–1.89 | VW |
| 13,1,1;11,7,1;11,5,5;993 | 168,171 | 1.92–1.89 | VW |
| 13,3,1;11,7,3;977 | 179 | 1.86–1.83 | VW |
| 13,3,3;995 | 187,192 | 1.82–1.79 | VW |
| 888 | 187,192 | 1.82–1.79 | VW |

TABLE E-continued

X-RAY DIFFRACTION PATTERN FOR ZEOLITE Y

| hkl | $h^2 + k^2 + l^2$ | d,Å | Relative Intensity |
|---|---|---|---|
| 13,5,1;11,7,5 | 195 | 1.78–176 | VW |
| 14,2,0;10,10,0;10,8,6 | 200 | 1.76–1.73 | W |
| 13,5,4;11,8,5 | 210 | 1.71–1.69 | W |

Occasionally, additional lines not belonging to the pattern for the zeolite appear in a pattern along with the x-ray lines characteristic of that zeolite. This is an indication that one or more additional crystalline materials are mixed with the zeolite in the sample being tested. Frequently these additional materials can be identified as initial reactants in the synthesis of the zeolite, or as other crystalline substances. When the zeolite is heat treated at temperatures of between 100° and 600° C. in the presence of water vapor or other gases or vapors, the relative intensities of the lines in the X-ray pattern may be appreciably changed from those existing in the unactivated zeolite patterns. Small changes in line positions may also occur under these conditions. These changes in no way hinder the identification of these X-ray patterns as belonging to the zeolite.

The particular X-ray technique and/or apparatus employed, the humidity, the temperature, the orientation of the powder crystals and other variables, all of which are well known and understood to those skilled in the art of X-ray crystallography or diffraction can cause some variations in the intensities and positions of the lines. These changes, even in those few instances where they become large, pose no problem to the skilled X-ray crystallographer in establishing identities. Thus, the X-ray data given herein to identify the lattice for a zeolite, are not to exclude those materials, which, due to some variable mentioned or otherwise known to those skilled in the art, fail to show all of the lines, or show a few extra ones that are permissible in the cubic system of that zeolite, or show a slight shift in position of the lines, so as to give a slightly larger or smaller lattice parameter.

A simple test described in "American Minerologist," vol. 28, page 545, 1943, permits a quick check of the silicon to aluminum ratio of the zeolite. According to the description of the test, zeolite minerals with a three dimensional network that contains aluminum and silicon atoms in an atomic ratio of Al/Si=2/3=0.67, or greater, produce a gel when treated with hydrochloric acid. Zeolites having smaller aluminum to silicon ratios disintegrate in the presence of hydrochloric acid and precipitate silica.

The zeolites contemplated herein exhibit adsorbtive properties that are unique among known adsorbents. The common adsorbents, like charcoal and silica gel, show adsorption selectivities based primarily on the boiling point or critical temperature of the adsorbate. Activated zeolites on the other hand, exhibits a selectivity based on the size and shape of the adsorbate molecule. Among those adsorbate molecules, whose size and shape are such as to permit adsorption by zeolites, a very strong preference is exhibited toward those that are polar, polarizable, and unsaturated. Another property of zeolites that contributes to its unique position among adsorbents is that of adsorbing large quantities of adsorbate at either very low pressures, at very low pressures, or at very low concentrations. One or a combination of one or more of these adsorption characteristics or others can make zeolites useful for numerous gas or liquid separation processes where adsorbents are not now employed. The use of zeolites permits more efficient and more economical operation of numerous processes now employing other adsorbents.

Common adsorbents like silica gel and charcoal do not exhibit any appreciable molecular sieve action, whereas the various forms of zeolites do. The sieving action of zeolite Z is shown by the following table in which $P_o$ represents the vapor pressure of the adsorbate at 25° C. In this table as well as others in the specification the term "weight % adsorbed" refers to the percentage increase in the weight of the adsorbent. The adsorbents were activated by heating them at a reduced pressure to remove adsorbed materials. Throughout the specification the activation temperature for zeolite X was 350° C., and the pressure at which it was heated was less than about 0.1 millimeter of mercury absolute unless otherwise specified. Likewise, the pressure given for each adsorption is the pressure of the adsorbate under the adsorption conditions unless the contrary is specified.

TABLE F
ADSORPTION DATA FOR ZEOLITE X

| Adsorbate | Temp. (°C.) | Pressure (mm. Hg) | Weight Percent Adsorbed |
| --- | --- | --- | --- |
| Octane | 25 | 11 | 30.0 |
| Benzene | 25 | 45 | 25.0 |
| m-Dichlorobenzene | 25 | $P_o$ | 35.5 |
| Heptacosafluorotributylamine | 23 | $P_o$ | 2.2 |

These data show that the porous structure of sodium zeolite X will permit free access to octane, benzene and dichlorobenzene molecules, so that they are readily adsorbed. But zeolite X is shown not to permit entry of the heptacosafluorotributylamine. This adsorptive behavior permits the separation of mixtures of heptacosafluorotributylamine and larger molecules from benzene, toluene, octane or other molecular species small enough to be adsorbed.

At about room temperature the sodium zeolite A adsorbs the C1 and C2 members of the straight chain saturated hydrocarbon series but not appreciable amounts of the higher homologs. Typical results are shown below.

TABLE G
ADSORPTION DATA FOR ZEOLITE A

| Adsorbate | Temp. (°C.) | Pressure (mm. Hg) | Weight Percent Adsorbed |
| --- | --- | --- | --- |
| Methane | 25 | 700 | 1.6 |
| Ethane | 25 | 700 | 7.4 |
| Propane | 25 | 700 | 0.7 |
| Butane | 25 | 132 | 0.9 |
| Octane | 25 | 12 | 0.5 |

This data suggests a process of using sodium zeolite A to remove methane and ethane from mixtures with propane and higher homologs of the series and with other larger molecules not appreciably adsorbed or with other gases less strongly adsorbed. The maximum dimension for ethane is 4.0 Å, and for propane 4.9 Å. The sodium zeolite A adsorbs the former but not appreciable amounts of the latter.

Zeolite Y has been found to have particularly good adsorption characteristics as is demonstrated by the representative adsorption data in Table H.

TABLE H
ADSORBATE DATA FOR ZEOLITE Y

| Adsorbate | Pressure (mm. Hg) | Temp. (°C.) | Weight Percent Adsorbed |
| --- | --- | --- | --- |
| $H_2O$ | 25 | 25 | 35.2 |
| $CO_2$ | 700 | 25 | 26.0 |
| n-pentane | 200 | 25 | 14.9 |
| $(C_4F_9)_3N$ | 0.07 | 25 | 1.1 |
| $(C_4F_9)_3N$ | 0.5 | 50 | 21.4 |
| Krypton | 20 | −183 | 70.0 |
| Oxygen | 700 | −183 | 35.7 |

These data were obtained in the following manner:

Samples of zeolite Y which had been activated by dehydration at a temperature of approximately 350° C., under vacuum, were tested to determine their adsorption properties. The adsorption properties were measured in a McBain-Baker adsorption system. The zeolite samples were placed in light aluminum buckets suspended from quartz springs. They were activated in situ, and the gas or vapor under test was then admitted to the system. The gain in weight of the adsorbent was measured by the spring extensions as read by a cathetometer. In Table H the pressure given for each adsorption is the pressure of the adsorbate. The term "weight percent adsorbed" in the table refers to the percentage increase in the weight of the activated adsorbent.

As may be seen from the adsorption data in Table H, activated zeolite Y can be employed to separate molecules having a critical dimension greater than that of heptocosafluorotributylamine from molecules having smaller critical dimensions. The critical dimension of a molecule is defined as the diameter of the smallest cylinder which will accomodate a model of the molecule constructed using the best available van der Waals radii, bond angles, and bond lengths.

A unique property of zeolite Y is its strong preference for polar, polarizable and unsaturated molecules, providing, of course, that these molecules are of a size and shape which permits them to enter the pore system. This is in contrast to charcoal and silica gel which show a primary preference based on the volatility of the adsorbate.

The reactivation or regeneration methods that may be used with zeolite Y differ from those used for the common adsorbents. Under the conditions of activation, reactivation or regeneration found to be satisfactory for zeolite Y, most other common adsorbents are either partially or completely destroyed by the heat or oxidized by the air. The conditions used for desorption of an adsorbate from zeolite Y vary with the adsorbate, but either one or a combination of raising the temperature and reducing the pressure, partial pressure or concentration of the adsorbate in contact with the adsorbent is usually employed. Another method is the displacement of the adsorbate by adsorption of another more strongly held adsorbate. For example, the desorption of occluded molecules from zeolite Y may be effected by washing with water or steam or by purging with a gas while heating, or by vacuum treatment.

Zeolite Y is distinguished from other molecular sieve types, for example, zeolite X described in U.S. Pat. No. 2,882,244, by its exceptional stability toward steam at elevated temperatures. This is a property which makes zeolite Y particularly suitable for such processes as gas drying, especially where the adsorbent bed must withstand numerous adsorption-desorption cycles. Zeolite Y is hydrolytically more stable than zeolite X. To demonstrate the improved c stability afforded by zeolite Y, the data of Table I are presented. The relative hydrolytic stability was determined by measurement of the oxygen adsorption capacities of zeolite Y and zeolite before and after heating in the presence of saturated steam at 410° C. and atmospheric pressure for three hours.

TABLE I

COMPARISON OF ADSORPTION CAPACITIES
OF ZEOLITE X AND ZEOLITE Y

| Zeolitic Molecular Sieve | Molar $SiO_2/Al_2O_3$ Content | Percent of Original Oxygen Capacity Retained After Steaming* |
|---|---|---|
| X | 2.2 | 11 |
| X | 2.5 | 9 |
| X | 2.7 | 17.5 |
| Y | 3.4 | 72 |
| Y | 3.8 | 80 |
| Y | 4.4 | 81 |
| Y | 4.6 | 87 |
| Y | 5.1 | 97 |
| Y | 5.3 | 90 |

*Measured at −183° C. and 100 mm. Hg.

Another means of differentiating zeolite Y compositions having a product silica-to-alumina molar ratio greater than 3 up to about 6 from zeolite X is by examination of the electrical properties of the particular species. The specific conductivity at several temperatures, as determined from resistance measurements made with specially constructed A.C. impedance bridges, and the values of activation energy ($\Delta H$) required for ionic conductivity in sodium zeolite X and sodium zeolite Y compositions are given in Table J below.

TABLE J

| Zeolite Type and Molar $SiO_2/Al_2O_3$ Content | Specific Conductivity, $ohm^{-1} cm.^{-1}$ at temperature | | Activation Energy ($\Delta H$), Kcal./mole |
|---|---|---|---|
| | 143.6° C. | 282.5° C. | |
| X 2.4 | $2.0 \times 10^{-5}$ | $8.0 \times 10^{-4}$ | 12.0 |
| X 3.0 | $5.4 \times 10^{-6}$ | $2.1 \times 10^{-4}$ | 12.2 |
| Y 3.8 | $1.6 \times 10^{-6}$ | $9.0 \times 10^{-5}$ | 13.7 |
| Y 4.5 | $2.4 \times 10^{-7}$ | $2.4 \times 10^{-5}$ | 15.6 |
| Y 5.1 | $5.0 \times 10^{-8}$ | $5.0 \times 10^{-6}$ | 16.0 |
| Y 5.3 | — | $2.9 \times 10^{-6}$* | 16.3 |

*Measured at 298° C.

U.S. Pat. No. 2,882,243 describes a process for making zeolite A comprising preparing a sodium-aluminum-silicate water mixture having a $SiO_2/Al_2O_3$ mole ratio of from 0.5:1 to 2.5:1, a $Na_2O/SiO_2$ mole ratio of from 0.8:1 to 3:1, and a $H_2O/Na_2O$ mole ratio of from 35:1 to 200:1, maintaining the mixture at a temperature of from 20° to 175° C. until zeolite A is formed, and separating the zeolite A from the mother liquor.

U.S. Pat. No. 2,882,244 describes a process for making zeolite X comprising preparing a sodium-aluminum-silicate water mixture having a $SiO_2/Al_2O_3$ mole ratio of from 3:1 to 5:1, a $Na_2O/SiO_2$ mole ratio of from 1.2:1 to 1.5:1, and a $H_2O/Na_2O$ mole ratio of from 35:1 to 60:1, maintaining the mixture at a temperature of from 20° to 120° C. until zeolite X is formed, and separating the zeolite X from the mother liquor.

The process described in U.S. Pat. No. 3,101,251 is similar to that described in U.S. Pat. No. 2,882,243 and 2,882,244 except that the reaction mixture contains an admixture of non-kaolinitic alumino-silicate mineral and sodium hydroxide that has been fused at a temperature of between 330° and 370° C.

In U.S. Pat. No. 3,119,659, a kaolin clay and sodium hydroxide are formed into a compact body, dried, reacted in an aqueous mixture at a temperature of from 20° to 175° C. until a zeolite is formed. Zeolite A is formed in a reaction mixture having a $Na_2O/SiO_2$ molar ratio of 0.5:1 to 1.5:1, a $SiO_2/Al_2O_3$ molar ratio of 1.6:1 to 2.4:1 and a $H_2O/Na_2O$ molar ratio of 20:1 to 100:1. Zeolite X is formed in a reaction mixture having a $Na_2O/SiO_2$ molar ratio of 1.5:1, a $SiO_2/Al_2O_3$ molar ratio of 5:1, and a $H_2O/Na_2O$ molar ratio of 30:1 to 60:1. Zeolite Y is formed in a reaction mixture having a $Na_2O/SiO_2$ molar ratio of 0.5:1, a $SiO_2/Al_2O_3$ molar ratio of 7:1, and a $H_2O/Na_2O$ molar ratio of 20:1 to 40:1.

In U.S. Pat. No. 3,130,007 zeolite Y is formed by preparing an aqueous sodium alumino silicate mixture having a certain composition, maintaining the mixture at a temperature of 20° to 125° C. until zeolite Y is formed, and separating the zeolite Y from the mother liquor. Table K shows reaction mixture compositions that produce zeolite Y.

TABLE K

U.S. PAT. NO. 3,130,007
REACTION MIXTURE COMPOSITIONS FOR ZEOLITE Y

| $Na_2O/SiO_2$ | $SiO_2/Al_2O_3$ | $H_2O/Na_2O$ |
|---|---|---|
| 0.20–0.40 | 10–40 | 25–60 |
| 0.41–0.60 | 10–30 | 20–60 |
| 0.61–0.80 | 7–30 | 20–60 |
| 0.6–1.0 | 8–30 | 12–90 |
| 1.5–1.7 | 10–30 | 20–90 |
| 1.9–2.1 | 10 | 40–90 |

U.S. Pat. No. 3,130,007 indicates on column 2, lines 35–42 the necessity of using an active silica source by specifying that aqueous colloidal silica sols or reactive amorphous solid silicas are preferred.

In U.S. Pat. No. 4,016,246 zeolite Y is formed by preparing an aqueous alumino silicate reaction mixture by mixing an alumina component and a $Na_2O$ component with an active hydrate sodium metasilicate to form a certain reaction mixture, then heating the mixture at a temperature of 20° to 120° C. until zeolite Y is formed. Table L shows reaction mixture compositions that produce zeolite Y.

TABLE L

U.S. PAT. NO. 4,016,246
REACTION MIXTURE COMPOSITIONS FOR ZEOLITE Y

| $Na_2O/SiO_2$ | $SiO_2/Al_2O_3$ | $H_2O/Na_2O$ |
|---|---|---|
| 0.28–<0.30 | 8–10 | 20–70 |
| 0.30–<0.31 | 8–12 | 20–70 |
| 0.31–<0.32 | 8–14 | 20–70 |
| 0.32–<0.34 | 8–16 | 12–90 |
| 0.34–<0.40 | 7–40 | 12–120 |
| 0.4–<0.7 | 5–50 | 12–120 |
| 0.7– <1.0 | 31–50 | 12–120 |

U.S. Pat. No. 4,016,246 also discusses the significance of using an activated source of sodium silicate. In that patent, active hydrated sodium metasilicate is prepared by carefully hydrating sodium metasilicate under specified conditions.

From the prior art one would assume that zeolite A cannot be made from reaction mixtures having a $SiO_2/Al_2O_3$ molar ratio greater than 2.5:1; that zeolite X cannot be made from reaction mixtures having a $SiO_2/Al_2O_3$ molar ratio greater than 5:1; and that zeolite Y cannot be made from an unreactive source of silica.

Nothing in the prior art teaches that a combination of zeolite A and zeolite X can be formed in the same reaction.

BRIEF DESCRIPTION OF THE DRAWINGS

In order to facilitate the understanding of this invention, reference will now be made to the appended drawings. The drawings should not be construed as limiting the invention but are exemplary only.

SUMMARY OF THE INVENTION

Figure 1:
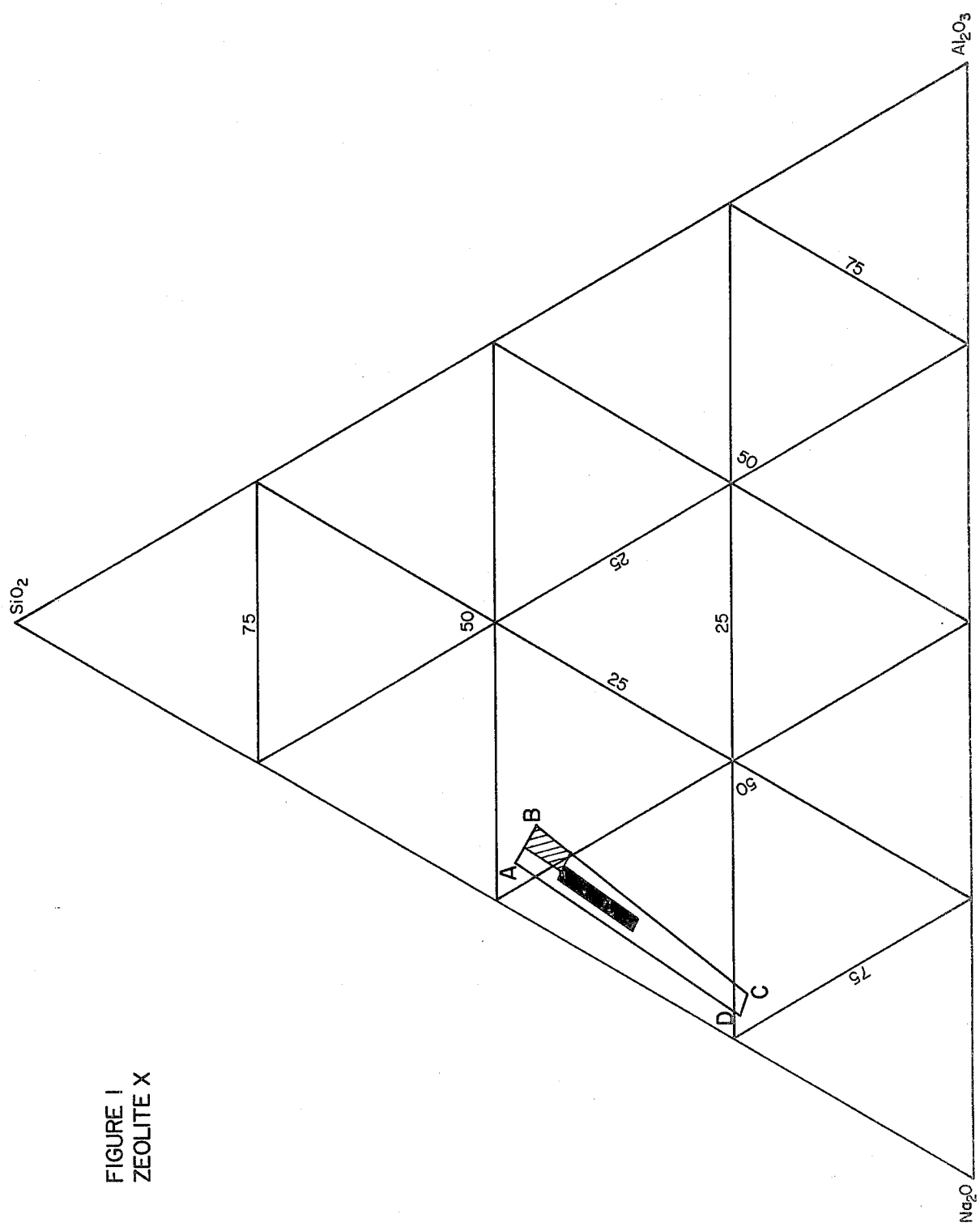
FIG. 1 shows the composition of the reaction mixture used in making zeolite X. The point A represents a composition having a $Na_2O/SiO_2$ ratio of 1:1 and a $SiO_2/Al_2O_3$ ratio of 1:1 and a $SiO_2/Al_2O_3$ ratio of 10:1. The point B represents a composition having a $Na_2O/SiO_2$ ratio of 1:1 and a $SiO_2/Al_2O_3$ ratio of 5:1 The point C represents a composition having a $Na_2O/SiO_2$ ratio of 3:1 and a $SiO_2/Al_2O_3$ ratio of 5:1. The point D represents a composition having a $Na_2O/SiO_2$ ratio of 3:1 and a $SiO_2/Al_2O_3$ ratio of 10:1.

Accordingly, it is an object of this invention to provide a new and highly effective process which overcomes the deficiencies of the prior art.

It is a further object of this invention to produce a zeolite using an inexpensive source of sodium silicate.

Another object of this invention is a process which can produce a zeolite in a relatively short period of time.

It is a further object of this invention to produce a very fine particle size zeolite without the use of mechanical methods such as high shear agitation or grinding of the product.

Another object of this invention is to provide a zeolite which has a very high exchange capacity for calcium and magnesium ions.

A further object of this invention is to produce a zeolite having a rapid calcium ion depletion rate.

Still another object of this invention is a method for producing a combination of zeolite X and zeolite A crystals of desirable proportions in the same batch.

Other objects and a fully understanding of the invention may be had by referring to the following description and claims taken in conjunction with the accompanying drawings.

In one embodiment of the present invention for the production of zeolite X, zeolite A or combinations thereof, the present invention achieves its objectives by forming a sodium aluminate solution, forming a sodium silicate solution, adding the sodium aluminate solution to the sodium silicate solution to form a reaction mixture comprising a sodium silicate mother liquor and an amorphous sodium alumino silicate pigment having a certain composition, heating the mixture to a temperature of from 80° to 120° C., preferably 100° C., reacting the mixture at a temperature of from 80° to 120° C., preferably 100° C., until a zeolite is formed, then recovering that zeolite. Both the sodium aluminate solution and the sodium silicate solution are preferably heated to a temperature of between 80° and 120° C. prior to the addition of the sodium aluminate to the sodium silicate, more preferably 90° C. Preferably the sodium silicate solution has a silica to sodium oxide molar ratio of about 2.4:1. Preferably the sodium aluminate solution is added to the sodium silicate solution so that all of the sodium aluminate solution is added within 30 seconds. The sodium silicate mother liquor can be recycled as a source of sodium silicate solution.

Zeolite X is formed when the reaction mixture has a sodium oxide to silica molar ratio of between 1:1 and 3:1, preferably between 1.2:1 and 1.7:1, most preferably about 1.6:1, a silica to alumina molar ratio of between 5:1 and 10:1, preferably between 6:1 and 8:1, most preferably about 7.3:1; and a water to sodium oxide molar ratio of between 25:1 and 90:1, preferably between 30:1 and 60:1, most preferably about 30:1. This material has a calcium carbonate exchange capacity greater than 230 mg $CaCO_3$/g zeolite and a magnesium carbonate exchange capacity greater than 135 mg $MgCO_3$/g zeolite. It is useful as an ion exchange material in water softening compositions and detergents; as a filler in paper, rubber and plastics; as a thickener in dentifrices; and as a non-settling flatting pigment in paints.

Zeolite A is formed when the reaction mixture has a sodium oxide to silica molar ratio of between 1:1 and 2.5:1, preferably between 1.5:1 and 2:1, most preferably about 1.5:1; a silica to alumina molar ratio of between 3:1 and 10:1, preferably between 4:1 and 8:1, most preferably about 7.3:1; and a water to sodium oxide molar ratio of between 10:1 and 35:1, preferably between 15:1 and 20:1, most preferably about 20:1. The particle size of zeolite A may be controlled by adjusting the silica to alumina molar ratio, with the particle size decreasing as the silica to alumina molar ratio is increased and the particle size increasing as the silica to alumina molar ratio is decreased. This material has a calcium carbonate exchange capacity greater than 250 mg $CaCO_3$/g zeolite and a magnesium carbonate exchange capacity greater than 140 mg $MgCO_3$/g zeolite. It is useful as an ion exchange material in water softening compositions and detergents; as a filler in paper, rubber and plastics;

as a thickener in dentifrices; and as a non-settling flatting pigment in paints.

A combination of from 20 to 80% zeolite X and from 20 to 80% zeolite A is formed when the reaction mixture has a sodium oxide to silica molar ratio of between 0.5:1 and 3:1, preferably between 1.4:1 and 3:1, more preferably between 1.6:1 and 2:1, most preferably about 1.7:1; a silica to alumina molar ratio of between 2:1 and 15:1, preferably between 2:1 and 10:1, more preferably between 2:1 and 8:1, most preferably about 5.3:1; and a water to sodium oxide molar ratio of between 10:1 and 60:1, preferably between 20:1 and 50:1, more preferably between 25:1 and 35:1, most preferably about 30:1. The material has a calcium carbonate exchange capacity greater than 230 mg $CaCO_3$/g zeolite and a magnesium carbonate exchange capacity greater than 135 mg $MgCO_3$/g zeolite. It is useful as an ion exchange material in water softening compositions and detergents; as a filler in paper, rubber and plastics; as a thickener in dentifrices; and as a non-settling flatting pigment in paints.

In another embodiment of the present invention for the production of zeolite X, zeolite A or combinations thereof, the present invention achieves its objectives by dissolving sand in a sodium hydroxide solution at a pressure of at least 100 psig heated to a temperature of at least 130° C. to produce a sodium silicate solution having a silica to sodium oxide molar ratio of between 2.4:1 and 2.8:1, activating the sodium silicate thus formed with alumina, forming a sodium aluminate solution, adding the sodium aluminate solution to the sodium silicate solution so that all of the sodium aluminate solution is added within 30 seconds to form a reaction mixture comprising a sodium silicate mother liquor and an amorphous sodium alumino silicate pigment having, in total, a certain composition, heating the mixture to a temperature of from 80° to 120° C., reacting the mixture at a temperature of from 80° to 120° C., then recovering the zeolite produced. Preferably the sodium silicate solution has a silica to sodium oxide molar ratio of about 2.4:1. The sodium silicate is activated with from 50 to 2000 ppm alumina at a temperature of from 15° to 100° C. for at least 10 minutes, preferably with from 400 to 600 ppm alumina at room temperature, most preferably with about 600 ppm alumina. Both the sodium silicate solution and the sodium aluminate solution are heated to a temperature of between 80° to 120° C., preferably 90° C., prior to the addition of the sodium aluminate to the sodium silicate. The reaction mixture is reacted at a temperature of from 80° to 120° C. until a zeolite is formed, preferably at a temperature of from 80° to 100° C., most preferably at a temperature of about 100° C. The sodium silicate mother liquor may be recycled as a source of sodium silicate solution.

Zeolite X is formed when the reaction mixture has a sodium oxide to silica molar ratio of between 1:1 and 1.2:1, preferably 1:1; a silica to alumina molar ratio of between 5:1 and 7:1, preferably 7:1; and a water to sodium oxide molar ratio of between 30:1 and 40:1, preferably about 30:1.

Zeolite A is formed when the reaction mixture has a sodium oxide to silica molar ratio of between 1.4:1 and 2:1, preferably about 1.8:1; a silica to alumina molar ratio of between 3:1 and 7:1, preferably about 7:1; and a water to sodium oxide molar ratio of between 25:1 and 35:1, preferably about 30:1.

A combination of from 20 to 80% zeolite X and from 20 to 80% zeolite A is formed when the reaction mixture has a sodium oxide to silica molar ratio of between 0.5:1 and 2.5:1, preferably between 0.7:1 and 1.7:1, more preferably about 0.7:1; a silica to alumina molar ratio of between 5:1 and 15:1, preferably between 5:1 and 10:1, more preferably about 9.8:1; and a water to sodium oxide molar ratio of between 10:1 and 60:1, preferably between 15:1 and 60:1, more preferably about 15.8:1.

In the production of zeolite Y, the present invention overcomes the deficiencies of the prior art and achieves its objectives by dissolving sand in a sodium hydroxide solution at a pressure of at least 100 psig, preferably 140 psig; heated to a temperature of at least 130° C., activating the sodium silicate thus formed with alumina, forming a sodium aluminate solution, adding sodium aluminate solution to the sodium silicate solution so that all of the sodium aluminate solution is added within 30 seconds to form a reaction mixture comprising a sodium silicate mother liquor and an amorphous sodium alumino silicate pigment having, in total, a certain composition, heating the mixture to a temperature of from 80° to 120° C., reacting the mixture at a temperature of from 80° to 120° C., then recovering the zeolite produced. The sodium silicate solution has a silica to sodium oxide molar ratio of between 2.4:1 and 2.8:1, preferably about 2.4:1. The sodium silicate is activated with from 50 to 2000 ppm alumina at a temperature of from 15° to 100° C. for at least 10 minutes, preferably with from 400 to 600 ppm alumina at room temperature, most preferably with about 500 ppm alumina. The sodium silicate solution is heated to a temperature of between 80° and 120° C., preferably 90° C. The sodium aluminate solution is also heated to a temperature of between 80° and 120° C., preferably 90° C. The composition of the reaction mixture has a sodium oxide to silica molar ratio of between 0.5 and 1.0:1, preferably about 0.56:1. It has a silica to alumina molar ratio of between 7:1 and 30:1, preferably between 7:1 and 10:1, and most preferably of about 7.8:1. The reaction mixture also has a water to sodium oxide molar ratio of between 10:1 and 90:1, preferably between 20:1 and 40:1 and most preferably of about 20:1. The reaction mixture is reacted at a temperature of from 80° to 120° C. until crystalline zeolite Y is formed, preferably at a temperature of from 80° to 100° C., most preferably at a temperature of about 100° C. The sodium silicate mother liquor may be recycled as a source of sodium silicate solution.

DESCRIPTION OF THE PREFERRED EMBODIMENTS

In its broadest aspect, the present invention is based upon the discovery that the type of zeolite formed is determined by how long it takes for the zeolite to be formed.

In the prior art processes for forming zeolites, a reaction mixture of sodium-aluminum-silicate water is prepared having a particular composition. This mixture is maintained at a certain temperature until crystals are formed, then the crystals are separated from the reaction mixture. For silica to alumina molar ratios greater than two, the reaction mixture consists of a sodium silicate mother liquor and an amorphous sodium alumino silicate pigment. When this two phase reaction mixture is reacted at elevated temperatures, nothing visually happens for a certain period of time, but after that period of time the zeolite rapidly crystallizes and can then be separated from the reaction mixture.

The present invention is based upon the discovery that, for any particular source of silica, the type of zeolite formed is determined by the reaction time necessary for the beginning of crystallization to occur. When the reaction time is short, hydroxysodalite is formed, but if the reaction time is longer, zeolite Z is formed. If the reaction time is still longer, zeolite X is formed. Zeolite Y is formed for reaction times longer than required for zeolite X. When the reaction time is between that necessary for the formation of zeolite X and that necessary for the formation of zeolite A, then a combination of zeolite X and zeolite A is formed. The reaction time is dependent upon the source of silica and whether or not the silica has been activated. The reaction time can be found readily by experimentation for any particular source of silica.

The reaction time necessary for crystallization can be controlled in a variety of ways, but the major way of controlling reaction time is by adjusting the water to sodium oxide molar ratio of the reaction mixture. The reaction time necessary to form a zeolite is directly proportional to the water to sodium oxide molar ratio used. For instance, when the source of silica is not activated with alumina, the preferred water to sodium oxide molar for making zeolite A is between 15:1 and 20:1; for making zeolite X, it is between 30:1 and 60:1; and for making a combination of zeolite X and zeolite A it is between 25:1 and 35:1. This is as one would expect because the higher water to sodium oxide ratio means a more dilute solution, which means that it takes longer for the reaction sites to come together. Therefore, to get a zeolite X in a reaction mixture having a sodium oxide to silica molar ratio and a silica to alumina molar ratio where normally a zeolite Y would be formed, one would decrease the water to sodium oxide ratio. Adjusting the water to sodium oxide molar ratio is the main control for determining which type of zeolite is formed and is analogous to a course control on a proportional feedback controller.

This relationship between the water to sodium oxide molar ratio and the type of zeolite formed is not shown in the prior art. For instance, U.S. Pat. Nos. 2,882,243 and 2,882,244, both issued to Robert Milton, show a water to sodium oxide molar ratio of from 35 to 200 for the production of zeolite A and a water to sodium oxide molar ratio of from 35 to 60 for the production of zeolite X. In U.S. Pat. No. 3,119,659, the water to sodium oxide molar ratio for the production of zeolite A is from 20 to 100 while the water to sodium oxide molar ratio for the production of zeolite X is from 30 to 60. None of the prior art show that the water to sodium oxide molar ratio should be higher for making zeolite X than for making zeolite A.

Another way of controlling the reaction time necessary for crystallization is by adjusting the sodium oxide to silica molar ratio of the reaction mixture. The reaction time necessary to form a zeolite is inversely proportional to the sodium oxide to silica molar ratio used. The effect of sodium oxide to silica molar ratio is less pronounced than that of water to sodium oxide molar ratio. It is analogous to a fine control on a proportional feedback controller.

One possible theory as to why increasing the sodium oxide to silica molar ratio would decrease the reaction time necessary to form a zeolite is that increasing the sodium oxide to silica molar ratio for a given water to sodium oxide molar ratio reduces the viscosity of the reaction mixture.

Adjusting the silica to alumina molar ratio of the reaction mixture also affects the reaction time necessary for crystallization, but this effect is much less than the effect of sodium oxide to silica molar ratio, which in turn is much less than the effect of water to sodium oxide molar ratio. For a given water to sodium oxide molar ratio and a given sodium oxide to silica molar ratio, the reaction time necessary to form a zeolite is directly proportional to the silica to alumina molar ratio.

The reaction time necessary for crystallization can also be increased by agitating the reaction mixture. The reaction time can be reduced by adding the sodium aluminate solution to the sodium silicate solution at a fast rate of addition, preferably so that all of the sodium aluminate solution is added within 30 seconds, and more preferably simultaneously. Thus, the reaction time necessary for crystallization can be increased by increasing the water to sodium oxide ratio; decreasing the sodium oxide to silicon dioxide molar ratio; increasing the silicon oxide to aluminum oxide molar ratio, agitating the reaction mixture and adding the two materials at a slow rate of addition.

Much more important than the effect of silica to alumina molar ratio on reaction time is the effect of silica to alumina molar ratio on particle size. The reason for this effect is not known but the particle size of a zeolite increases as the silica to alumina molar ratio of the reaction mixture approaches that of the desired zeolite. The particle size decreases as the silica to alumina molar ratio departs from that of the desired zeolite. For instance, the silica to alumina molar ratio of zeolite A is $1.85 \pm 0.5$. Therefore, a zeolite A formed in a reaction mixture having a silica to alumina molar ratio of 10:1 would have a smaller particle size than a zeolite A formed in a reaction mixture having a silica to alumina molar ratio of 3:1. This means that one can control the particle size of a zeolite by adjusting the silica to alumina molar ratio of the reaction mixture. In order to increase particle size one would adjust the silica to alumina molar ratio of the reaction mixture so that it approaches the silica to alumina molar ratio of the desired product. For zeolite A, that ratio is $1.85 \pm 0.5$. For zeolite X it is $2.5 \pm 0.5$. For zeolite Y it is $4.5 \pm 1.5$. In order to decrease particle size one would adjust the silica to alumina molar ratio of the reaction mixture so that it departs from the silica to alumina molar ratio of the desired product.

For both zeolite X and zeolite A, the silica to alumina molar ratios of the reaction mixtures used in the present invention are higher than the silica to alumina molar ratios of the desired product. Therefore, to increase the particle size of either zeolite X or zeolite A or a combination thereof, one would decrease the silica to alumina molar ratio of the reaction mixture. In order to decrease the particle size, one would increase the silica to alumina molar ratio of the reaction mixture.

The sodium oxide to silica molar ratio of the reaction mixture also affects the particle size of the final product, but this effect is much smaller in magnitude than the effect of silica to alumina molar ratio. For a constant silica to alumina molar ratio, the particle size is inversely proportional to sodium oxide to silica molar ratio. As the sodium oxide to silica molar ratio increases, the particle size decreases. As the sodium oxide to silica molar ratio decreases, the particle size increases. Thus, the effect of sodium oxide to silica molar ratio of the reaction mixture on particle size can be used in combination with the effect of silica to alumina molar ratio of the reaction mixture on particle size as a means of controlling particle size.

In the present invention, a zeolite is formed by forming a sodium aluminate solution, forming a sodium silicate solution, adding the sodium aluminate solution to the sodium silicate solution to produce a reaction mixture comprising a sodium silicate mother liquor and an amorphous sodium alumino silicate pigment, heating the mixture to a temperature of from 80° to 120° C., reacting the mixture at a temperature of from 80° to 120° C. until the desired zeolite is formed, and recovering the desired zeolite from the mother liquor.

The sodium silicate solution used in this process can be formed by dissolving sand in a sodium hydroxide solution at a pressure of at least 100 psig and a temperature of at least 130° C. to produce a sodium silicate solution having a silica to sodium oxide molar ratio of between 2.4:1 and 2.8:1. This sodium silicate solution is activated with from 50 to 2000 ppm alumina at a temperature of between 15° and 100° C. for at least 10 minutes and heated to a temperature between 80° and 120° C.

Zeolite X can be formed in a reaction medium having a sodium oxide to silica molar ratio of between 1:1 and 3:1; and a silica to alumina molar ratio of between 5:1 and 10:1. This reaction mixture is represented in FIG. 1 by the area ABCD. When the sodium silicate source has been activated with alumina, the preferred reaction mixture has a sodium oxide to silica molar ratio of between 1:1 and 1.2:1 and a silica to alumina molar ratio of between 5:1 and 7:1. This reaction mixture is represented in FIG. 1 by the area having diagonal hatching. When the sodium silicate source has not been activated with alumina, the preferred reaction mixture has a sodium oxide to silica molar ratio of between 1.2:1 and 1.7:1 and a silica to alumina molar ratio of between 6:1 and 8:1. This reaction mixture is represented in FIG. 1 by the shaded area.

Figure 2:
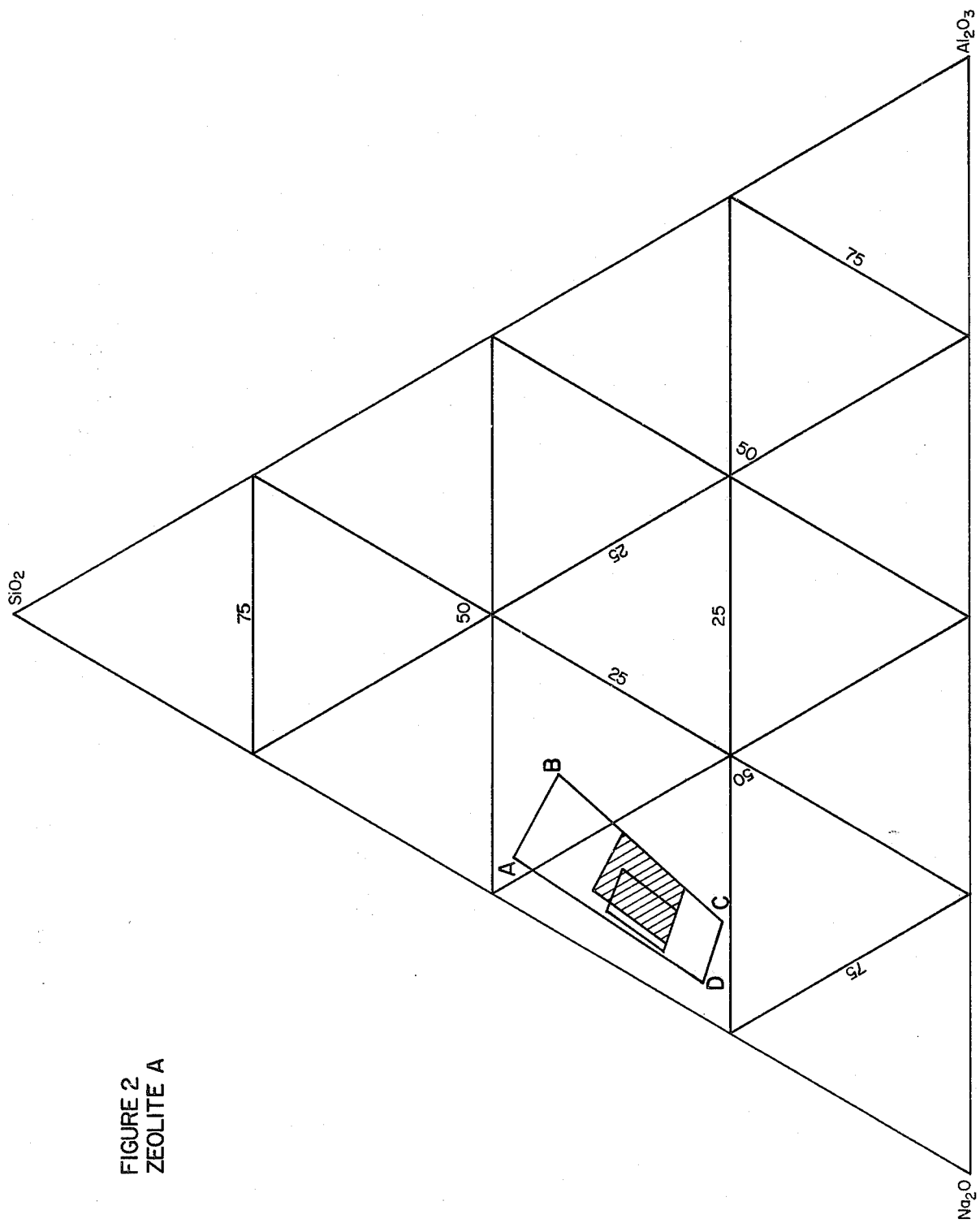
FIG. 2 shows the composition of the reaction mixture used in making zeolite A. The point A represents a composition having a $Na_2O/SiO_2$ ratio of 1:1 and a $SiO_2/Al_2O_3$ ratio of 35:1. The point B represents a composition having a $Na_2O/SiO_2$ ratio of 1:1 and a $SiO_2/Al_2O_3$ ratio of 10:1. The point C represents a composition having a $Na_2O/SiO_2$ ratio of 2.5:1 and a $SiO_2/Al_2O_3$ ratio of 10:1. The point D represents a composition having a $Na_2O/SiO_2$ ratio of 2.5:1 and a $SiO_2/Al_2O_3$ ratio of 35:1.

Zeolite A can be formed in a reaction mixture having a sodium oxide to silica molar ratio of between 1:1 and 2.5:1; and a silica to alumina molar ratio of between 3:1 and 10:1. This reaction mixture is represented in FIG. 2 by the area ABCD. When the sodium silicate source has been activated with alumina, the preferred reaction mixture has a sodium oxide to silica molar ratio of between 1.4:1 and 2:1; and a silica to alumina molar ratio of between 3:1 and 7:1. This reaction mixture is represented in FIG. 2 by the area having diagonal hatching. When the sodium silicate source has not been activated with alumina, the preferred reaction mixture has a sodium oxide to silica molar ratio of between 1.5:1 and 2:1; and a silica to alumina molar ratio of between 4:1 and 8:1. This reaction mixture is represented in FIG. 2 by the shaded area.

Figure 3:
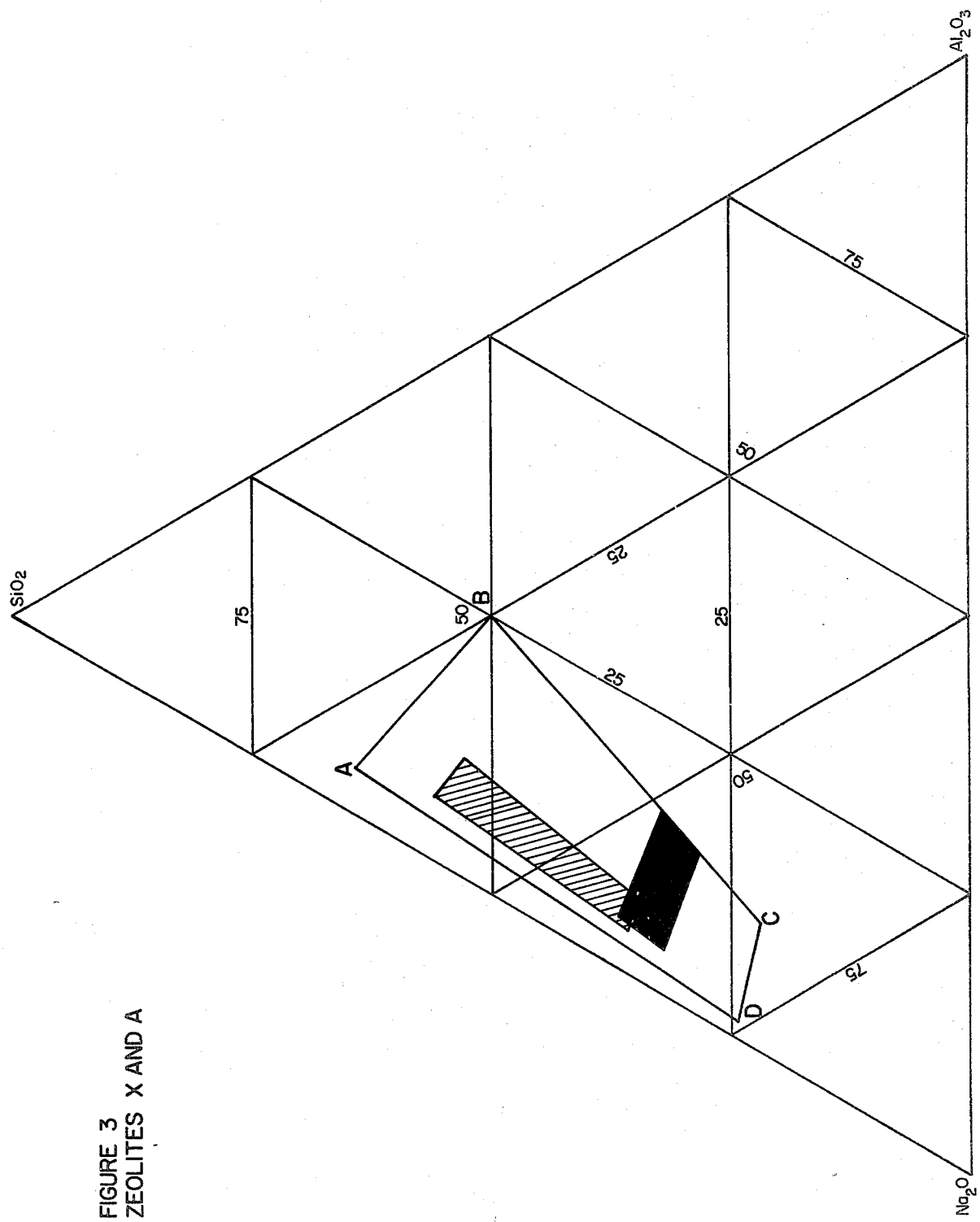
FIG. 3 shows the composition of the reaction mixture used in making a combination of zeolite X and zeolite A. The point A represents a composition having a $Na_2O/SiO_2$ ratio of 0.5:1 and a $SiO_2/Al_2O_3$ ratio of 60:1. The point B represents a composition having a $Na_2O/SiO_2$ ratio of 0.5:1 and a $SiO_2/Al_2O_3$ ratio of 10:1. The point C represents a composition having a $Na_2O/SiO_2$ ratio of 3:1 and a $SiO_2/Al_2O_3$ ratio of 10:1. The point D represents a composition having a $Na_2O/SiO_2$ ratio of 3:1 and a $SiO_2/Al_2O_3$ ratio of 60:1.

A combination of zeolite X and zeolite A can be formed in a reaction mixture having a sodium oxide to silica molar ratio of between 0.5:1 and 3:1; and a silica to alumina molar ratio of between 2:1 and 15:1. This reaction mixture is represented in FIG. 3 by the area ABCD. When the sodium silicate source has been activated with alumina, the preferred reaction mixture has a sodium oxide to silica molar ratio of between 0.7:1 and 1.7:1; and a silica to alumina molar ratio of between 5:1 and 10:1. This reaction mixture is represented in FIG. 3 by the area having diagonal hatching. When the sodium silicate source has not been activated with alumina, the preferred reaction has a sodium oxide to silica molar ratio of between 1.6:1 and 2:1, and a silicate to alumina molar ratio of between 2:1 and 8:1. This reaction mixture is represented in FIG. 3 by the shaded area.

Figure 4:
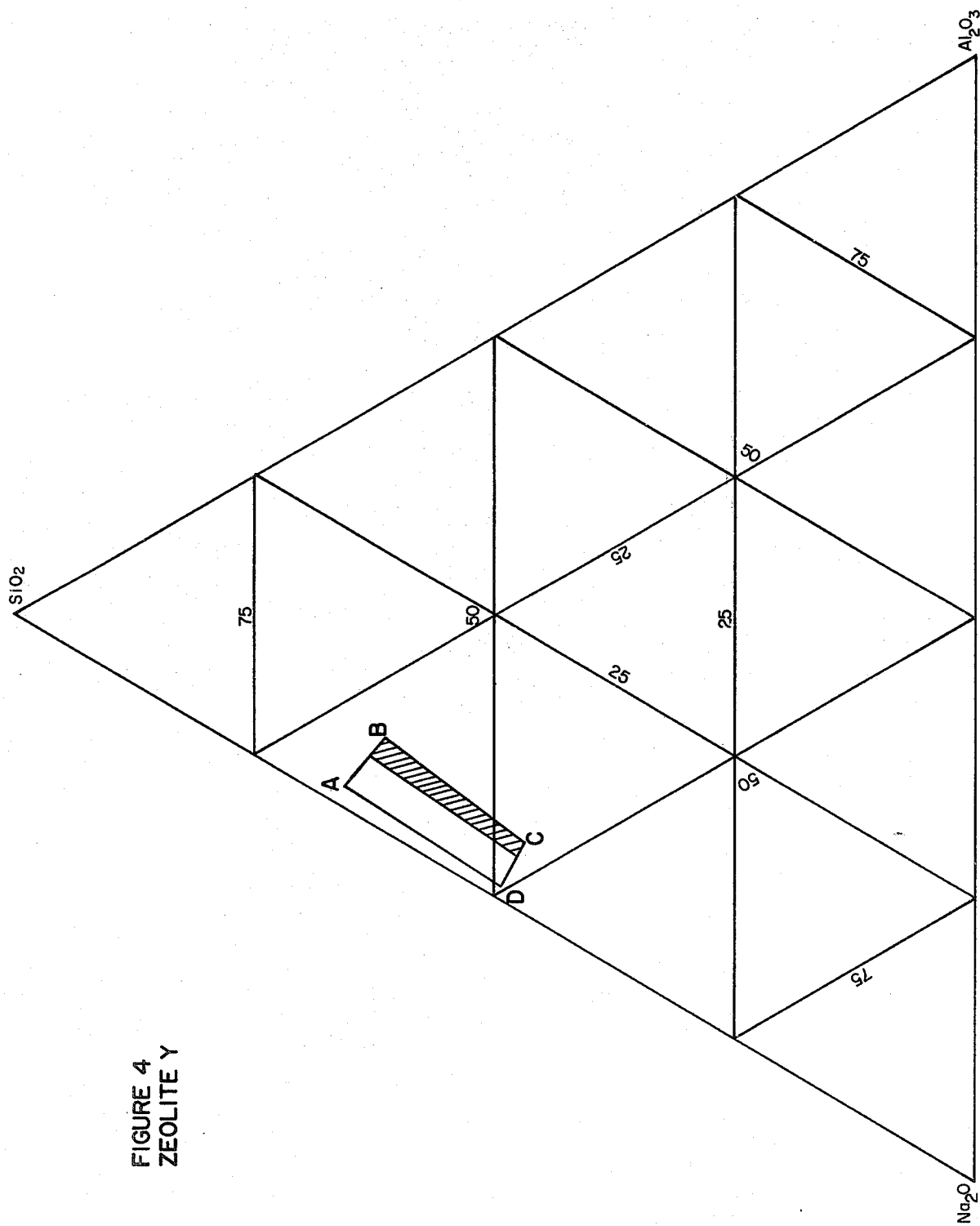
FIG. 4 shows the composition of the reaction mixture used in making zeolite Y. The point A represents a composition having a $Na_2O/SiO_2$ ratio of 0.5:1 and a $SiO_2/Al_2O_3$ ratio of 30:1. The point B represents a composition having a $Na_2O/SiO_2$ ratio of 0.5:1 and a $SiO_2/Al_2O_3$ ratio of 7:1. The point C represents a composition having a $Na_2O_3/SiO_2$ ratio of 1:1 and a $SiO_2/Al_2O_3$ ratio of 7:1. The point D represents a composition having a $Na_2O/SiO_2$ ratio of 1:1 and a $SiO_2/Al_2O_3$ ratio of 30:1.

Zeolite Y can be formed from a sodium silicate source activated with alumina when the reaction mixture has a sodium oxide to silica molar ratio of between 0.5:1 and 1:1; and a silica to alumina molar ratio of between 7:1 and 30:1. This reaction mixture is represented in FIG. 4 by the area ABCD. The preferred reaction mixture has a sodium oxide to silica molar ratio of between 0.5:1 and 1:1, and a silica to alumina molar ratio of between 7:1 and 10:1. This reaction mixture is represented in FIG. 4 by the area having diagonal hatching.

The broad oxide mole ratio ranges for making each zeolite are shown in Table I.

TABLE I

| BROAD RANGES FOR MAKING ZEOLITES | | | |
|---|---|---|---|
| Zeolite | $Na_2O/SiO_2$ | $SiO_2/Al_2O_3$ | $H_2O/Na_2O$ |
| X | 1–3 | 5–10 | 25–90 |
| A | 1–2.5 | 3–10 | 10–35 |
| X & A | 0.5–3 | 2–15 | 10–60 |
| Y | 0.5–1 | 7–30 | 10–90 |

The preferred oxide mole ratio ranges for making each zeolite using a source of sodium silicate that has not been activated with alumina are shown in Table II.

TABLE II

| PREFERRED RANGES FOR MAKING ZEOLITES (Unactivated) | | | |
|---|---|---|---|
| Zeolite | $Na_2O/SiO_2$ | $SiO_2/Al_2O_3$ | $H_2O/Na_2O$ |
| X | 1.2–1.7 | 6–8 | 30–60 |
| A | 1.5–2 | 4–8 | 15–20 |
| X & A | 1.6–2 | 2–8 | 25–35 |

The preferred oxide mole ratio ranges for making each zeolite using a source of sodium silicate that has been activated with alumina are shown in Table III.

TABLE III

| PREFERRED RANGES FOR MAKING ZEOLITES (Activated) | | | |
|---|---|---|---|
| Zeolite | $Na_2O/SiO_2$ | $SiO_2/Al_2O_3$ | $H_2O/Na_2O$ |
| X | 1–1.2 | 5–7 | 30–40 |
| A | 1.4–2 | 3–7 | 25–35 |
| X & A | 0.7–1.7 | 5–10 | 15–60 |
| Y | 0.5–1 | 7–10 | 20–40 |

The reaction mixtures used in the present invention for producing zeolite X or zeolite A have higher silica to alumina molar ratios than the reaction mixtures used in the prior art for producing the same zeolite. For instance, in the present invention the silica to alumina molar ratio of the reaction mixture used to make zeolite X is between 5:1 and 10:1. In U.S. Pat. No. 2,882,244 zeolite X is made from a reaction mixture having a silica to alumina molar ratio of from 3:1 to 5:1. In the present invention, zeolite A is formed in a reaction mixture having a silica to alumina molar ratio of between 3:1 and 10:1. In U.S. Pat. No. 2,882,243 zeolite A is made from a reaction mixture having a silica to alumina molar ratio of from 0.5:1 to 2.5:1. Nothing in the prior art teaches that either zeolite X or zeolite A could be formed in a reaction mixture having such a high silica to alumina molar ratio as that of the present invention.

The silica to alumina molar ratio of zeolite X is about 2.5:1 and the silica to alumina molar ratio of zeolite A is about 1.85:1. Thus, the silica to alumina molar ratios of the reaction mixtures of the present invention are farther away from that of zeolite X or zeolite A than the silica to alumina molar ratios of the reaction mixtures of the prior art. As stated above, the particle size of the zeolite is smaller when the silica to alumina molar ratio of the reaction mixture is farther away from the silica to alumina molar ratio of the desired zeolite. Because of this, the zeolite X and the zeolite A of the present invention has a smaller particle size than that of the prior art.

Because of its small particle size, the zeolite X and the zeolite A of the present invention are both useful in a variety of uses such as an ion-exchange material in water softening compositions and detergents; as a filler in paper, rubber and plastics; as a thickener in dentifrices; and as a non-settling flatting pigment in paints.

These zeolites having smaller particle size have higher magnesium ion exchange capacities than zeolites having larger particle sizes. This increased magnesium ion exchange capacity makes these zeolites especially useful as ion exchange materials in water softening compositions and detergents.

Figure 5:
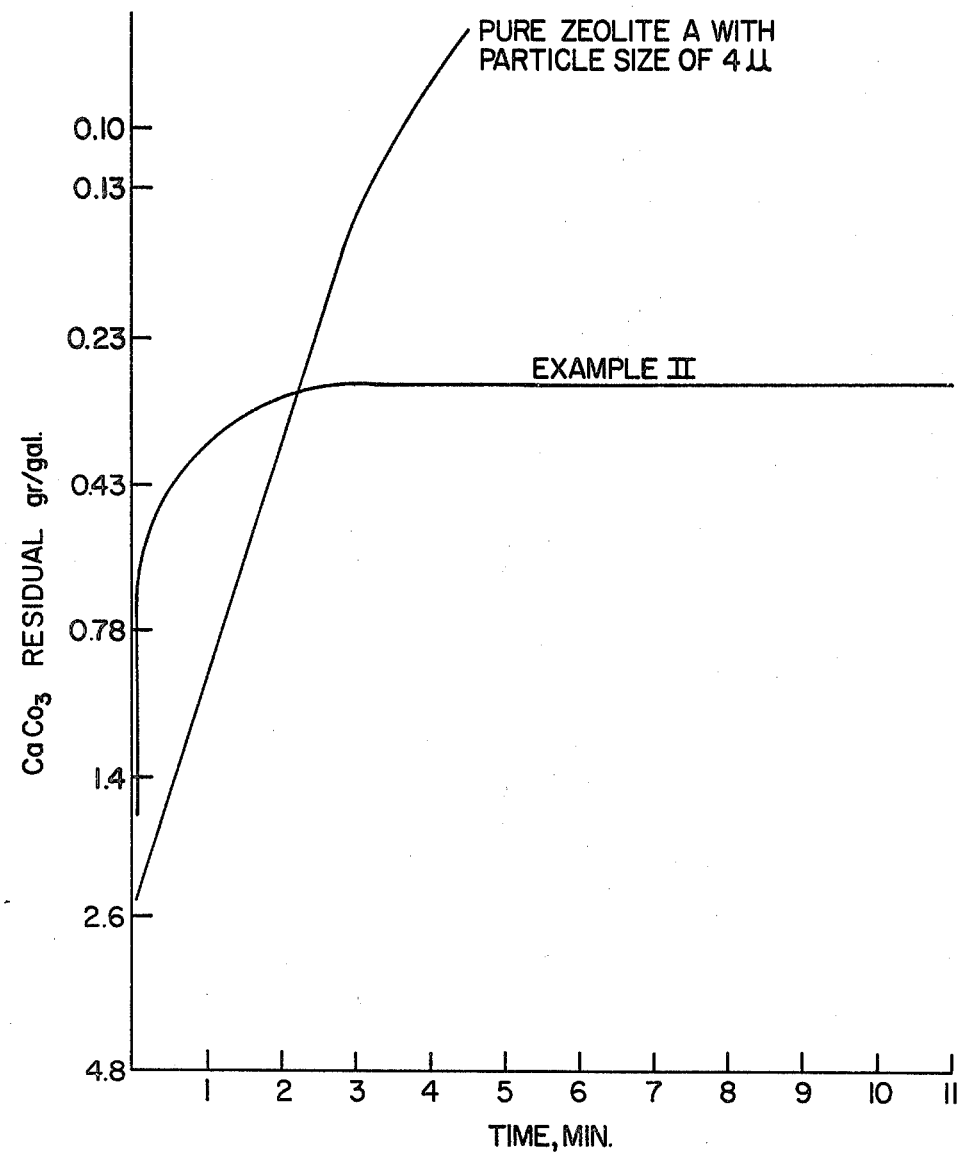
FIG. 5 shows the calcium carbonate depletion rate for Example II as compared to pure zeolite A with an average particle size of 4 microns.

Another factor that makes these zeolites especially useful as ion exchange materials is their fast calcium carbonate depletion rate. These zeolites remove calcium ions faster than zeolites having larger particle sizes. FIG. 5 shows the calcium carbonate depletion rate for a pure zeolite A having an average particle size of 4 microns and for Example II which is a pure zeolite A having an average particle size of 1.1 microns. The zeolite A having the smaller particle size adsorbs the calcium ions at a faster rate than the zeolite A having the larger particle size.

As can be seen in Tables I, II and III, the ranges of water to sodium oxide ratios needed to produce zeolite X, zeolite A, a combination of zeolite X and zeolite A or zeolite Y overlap with each other. The water to sodium oxide molar ratio is the major controlling factor which determines the reaction time necessary for crystallization, which in turn determines the type of zeolite formed. But, as stated above, there are other factors that have a smaller effect on reaction time, such as sodium oxide to silica molar ratio, silica to alumina molar ratio, degree of agitation and rate of addition of the sodium aluminate solution to the sodium silicate solution. These additional factors can either add to or subtract from the effect of water to sodium oxide molar ratio.

For instance, either zeolite X or zeolite A can be formed from a reaction mixture having a water to sodium oxide molar ratio of 30:1. In that case, the addition factors would determine which type of zeolite would be produced. If the sodium oxide to silica molar ratio is 1.2:1 and the silica to alumina molar ratio is 8:1, then zeolite X will probably be produced. But if the sodium oxide to silica molar ratio is 2:1 and the silica to alumina molar ratio is 3:1, then zeolite A will probably be produced. The type of zeolite formed depends on the total effect of the water to sodium oxide molar ratio and all of the additional factors mentioned above.

One of the results of using the principles of the present invention is the ability for the first time in history to make a controlled combination of zeolite X and zeolite A in the same reaction. A combination of from 20 to 80% zeolite X and from 20 to 80% zeolite A can be formed by adjusting the reaction time necessary for crystallization to a time between that required to make zeolite X and that required to make zeolite A. The composition of the combination depends on the reaction time. If the reaction time is close to that required to make zeolite X, much more zeolite X will be formed than zeolite A. If, on the other hand, the reaction time is close to that of zeolite A, much more zeolite A will be formed than zeolite X. By adjusting the reaction time, one can make any desired combination of zeolite X and zeolite A.

A combination of zeolite X and zeolite A can be formed in a reaction mixture having a sodium oxide to silica molar ratio of between 0.5:1 and 3:1; a silica to alumina molar ratio of between 2:1 and 15:1; and a water to sodium oxide molar ratio of between 10:1 and 60:1.

When the source of sodium silicate is not activated with alumina, the preferred reaction mixture for forming a combination of zeolite X and zeolite A has a sodium oxide to silica molar ratio of between 1.4:1 and 3:1; a silica to alumina molar ratio of between 2:1 and 10:1; and a water to sodium oxide molar ratio of between 20:1 and 50:1. More preferably, the reaction mixture should have a sodium oxide to silica molar ratio of between 1.6:1 and 2:1; a silica to alumina molar ratio of between 2:1 and 8:1; and a water to sodium oxide molar ratio of between 25:1 and 35:1.

When the source of sodium silicate has been activated with alumina, the preferred reaction mixture for forming a combination of zeolite X and zeolite A has a sodium oxide to silica molar ratio of between 0.5:1 and 2.5:1; a silica to alumina molar ratio of between 5:1 and 15:1; and a water to sodium oxide molar ratio of between 10:1 and 60:1. More preferably, the reaction mixture should have a sodium oxide to silica molar ratio of between 0.7:1 and 1.7:1; a silica to alumina molar ratio of between 5:1 and 10:1; and a water to sodium oxide molar ratio of between 15:1 and 60:1.

The combination of zeolite X and zeolite A has an average particle size less than 2 microns in diameter. It is useful, because of its small particle size, as an ion exchange material in water softening compositions and detergents; as a filler in paper, rubber and plastics; as a thickener in dentifrices; and as a non-settling flatting pigment in paints.

Any source of sodium silicate can be used in the present invention, but one particularly desirable source of sodium silicate is sand dissolved in caustic. The advantage of this source is its low cost. The sand is dissolved in a sodium hydroxide solution at a pressure of at least 100 psig and a temperature of at least 130° C. to produce a sodium silicate solution having a silica to sodium oxide molar ratio of between 2.4:1 and 2.8:1. Preferably the pressure is about 140 psig, producing a sodium silicate solution having a silica to sodium oxide molar ratio of about 2.4:1.

The time required to produce a given product such as zeolite Y from batches of identical chemical composition will be dependent on the source of silicon dioxide. Reactive silicas such as colloidal silica sols require less than 16 hours for a complete reaction. "Unreactive" sources of silica such as sodium silicate solution produced by dissolving sand in caustic require in excess of 100 hours to produce the same results. Each different type of silica source has its own time table specifying the reaction times needed to form each type of zeolite. One of the discoveries upon which this invention is based is the fact this time table can be changed by activating the silica source with alumina.

The silica source can be activated with from 50 to 2000 ppm alumina at a temperature of from 15° to 100° C. for at least 10 minutes. The alumina concentration limits of 50 to 2000 ppm alumina are critical values. For some reason, alumina concentrations outside these limits fail to activate the sodium silicate solution. Preferably, the alumina concentration is between 400 and 600 ppm, most preferably 600 ppm. Preferably the activation occurs at room temperature.

The alumina used to activate the sodium silicate solution may suitably be provided by a soluble aluminum compound such as sodium aluminate or a water soluble aluminum salt, such as aluminum sulphate. Sodiium aluminate is, however, the preferred reagent since it limits the tendency to introduce foreign ions into the zeolite lattice.

There is an important difference between the effect of activation and the effect of reaction time controlling factors such as water to sodium oxide molar ratio, sodium oxide to silica molar ratio, silica to alumina molar ratio, degree of agitation and rate of addition. The reaction time controlling factors are used to adjust the reaction time necessary for crystallization so that it will match with the reaction time in a time table to produce a particular zeolite. Activation changes the time table. For that reason, the preferred oxide ratios for producing a desired zeolite are different when a source of silica is either activated or not activated (See Tables II and III above).

After a sodium silicate solution is formed, and is either activated or not activated, a sodium aluminate solution is added to the sodium silicate solution to form a reaction mixture. Preferably both the sodium aluminate solution and the sodium silicate solution are heated to a temperature of between 80° and 120° C., more preferably 90° C. prior to the addition of the sodium aluminate to the sodium silicate.

The reaction mixture is heated to a temperature of from 80° to 120° C. and reacted at a temperature of from 80° to 120° C. until a zeolite is formed, preferably at a temperature of from 80° to 100° C., most preferably at a temperature of about 100° C. At lower temperatures, the crystals which form are smaller in size than those formed at the higher temperature.

To ensure a good yield of the desired zeolite product, it is necessary to react the zeolite mixture beyond a certain minimum time. If, however, the reaction is continued too long, the product starts to lose silica, that is the silica to alumina ratio starts to fall, and if the reaction is continued even further, then the product may recrystallize to an undesirable zeolitic material. There is an optimum reaction time which is, in part, determined by the ratios and concentrations of the original reaction time, by the size of the batch, the time required to mix the ingredients and the rate of heating. The optimum reaction time can readily be determined by experiment.

Once the zeolite has been separated from the sodium silicate mother liquor, the mother liquor may be recycled as a source of sodium silicate solution. Although it is possible to use the process of the present invention without recycling the mother liquor, failure to recycle the mother liquor could make the process cost prohibitive.

The invention will be further illustrated by the following examples which set forth particularly advantageous method and composition embodiments. While the examples illustrate the present invention, they are not intended to limit it.

EXAMPLE I

A sodium silicate solution of composition 3.2% sodium oxide and 7.7% silica was heated to 90° C. Sodium aluminate solution, also at 90° C., of composition 29% sodium oxide and 5.5% alumina was added to the sodium silicate so that all of the sodium aluminate solution was added within 30 seconds. The resulting gel was broken down by agitation until a homogeneous slurry was obtained. The batch was then reacted at 100° C. for 6 hours. The total batch composition had a sodium to silica molar ratio of about 1.6:1, a silica to alumina molar ratio of about 7.3:1 and a water to sodium oxide molar ratio of about 30:1. The resulting product was zeolite X which exhibited a calcium ion exchange capacity of 227 mg $CaCO_3$/g zeolite and a magnesium ion exchange capacity of 140 mg $MgCO_3$/g zeolite. The average particle size was 1.7 microns in diameter.

EXAMPLE II

A sodium silicate solution of composition 8% sodium oxide and 19% silica was heated to 90° C. Sodium aluminate solution, also at 90° C., of composition 17% sodium oxide and 3.6% alumina was added to the sodium silicate so that all of the sodium aluminate solution was added within 30 seconds. The resulting gel was broken down by agitation until a homogeneous slurry was obtained. The batch was then reacted at 100° C. for 2 hours. The total batch composition had a sodium oxide to silica molar ratio of about 1.5:1, a silica to alumina molar ratio of about 7.3:1 and a water to sodium oxide molar ratio of about 20:1. The resulting product was zeolite A which exhibited a calcium ion exchange capacity of 249 mg $CaCO_3$/g zeolite and a magnesium ion exchange capacity of 127 mg $MgCO_3$/g zeolite. The average particle size was 1.1 microns in diameter.

EXAMPLE III

A sodium silicate solution of composition 3.1% sodium oxide and 7.4% silica was heated to 90° C. Sodium aluminate solution, also at 90° C. of composition 27.3% sodium oxide and 6.5% alumina was added to the sodium silicate so that all of the sodium aluminate solution was added within 30 seconds. The resulting gel was broken down by agitation until a homogeneous slurry was obtained. The batch was then reacted at 100° C. for 4 hours. The total batch composition had a sodium oxide to silica molar ratio of about 1.7:1, a silica to alumina molar ratio of about 5.3:1 and a water to sodium oxide molar ratio of about 30:1. The resulting product was a combination of 53% zeolite X and 47% zeolite A, this product exhibits a calcium ion exchange capacity of 229 mg $CaCO_3$/g zeolite and a magnesium ion exchange capacity of 138 mg $MgCO_3$/g zeolite.

EXAMPLE IV

A sodium silicate solution of composition 4.2% sodium oxide and 10.2% silica was activated with 600 ppm alumina from a sodium aluminate solution. The sodium silicate solution was heated to 90° C. Sodium aluminate solution, also at 90° C., of composition 17% sodium oxide and 3.6% alumina was added to the sodium silicate so that all of the sodium aluminate solution was added within 30 seconds. The resulting gel was broken down by agitation until a homogeneous slurry was obtained. The batch was then reacted at 100° C. for 6 hours. The total batch composition had a sodium oxide to silica molar ratio of about 1:1, a silica to alumina molar ratio of about 7:1 and a water to sodium oxide molar ratio of about 30:1. The resulting product was zeolite X which exhibited both good calcium ion and magnesium ion exchange capacity.

EXAMPLE V

A sodium silicate solution of composition 8% sodium oxide and 19% silica was activated with 600 ppm alumina from a sodium aluminate solution. The sodium silicate solution was heated to 90° C. Sodium aluminate solution, also at 90° C., of composition 17% sodium oxide and a 3.6% alumina was added to the sodium silicate so that all of the sodium aluminate solution was added within 30 seconds. The resulting gel was broken down by agitation until a homogeneous slurry was obtained. The batch was then reacted at 100° C. for 6 hours. The total batch composition had a sodium oxide to silica molar ratio of about 1.8:1, a silica to alumina molar ratio of about 7:1 and a water to sodium oxide molar ratio of about 30:1. The resulting product was zeolite A which exhibited good calcium ion and magnesium ion exchange properties.

EXAMPLE VI

A sodium silicate solution of composition 11.23% sodium oxide and 27.15% silica was activated with 600 ppm alumina from a sodium aluminate solution. The sodium silicate was then heated to 65° C. for 30 minutes, then was heated to 90° C. At that time a sodium aluminate solution, also at 90° C., of composition 20% sodium oxide and 11% alumina was added to the sodium silicate so that all of the sodium aluminate solution was added within 30 seconds. The resulting gel was broken down by agitation until a homogeneous slurry was obtained. The batch was then reacted at 100° C. for 16 hours. The total batch composition had a sodium oxide to silica molar ratio of about 0.7:1, a silica to alumina molar ratio of about 9.8:1 and a water to sodium oxide molar ratio of about 15.8:1. The resulting product was a combination of 63% zeolite X and 37% zeolite A, this product exhibiting both good calcium ion and magnesium ion exchange capacity.

EXAMPLE VII

A sodium silicate solution of composition 11.2% sodium oxide and 27.15% silica was activated with 500 ppm alumina from a sodium aluminate solution. The sodium silicate was then heated to 90° C. for 30 minutes. At that time a sodium aluminate solution, also at 90° C., of composition 10.4% sodium oxide and 14.6% alumina was added to the sodium silicate so that all of the sodium aluminate solution was added within 30 seconds. The resulting gel was broken down by agitation until a homogeneous slurry was obtained. The batch was then reacted at 100° C. for 24 hours. The total batch composition had a sodium oxide to silica molar ratio of about 0.56:1, a silica to alumina molar ratio of about 7.8:1 and a water to sodium oxide molar ratio of about 20:1. The resulting product was zeolite Y with a silica to alumina molar ratio of 5.2:1.

The compositions of the reaction mixtures of Examples I–VII are summarized in Table IV.

TABLE IV

| Example | $Na_2O/SiO_2$ | $SiO_2/Al_2O_3$ | $H_2O/Na_2O$ | Type of Zeolite |
|---|---|---|---|---|
| I | 1.6 | 7.3 | 30 | X |
| II | 1.5 | 7.3 | 20 | A |

TABLE IV-continued

| Example | $Na_2O/SiO_2$ | $SiO_2/Al_2O_3$ | $H_2O/Na_2O$ | Type of Zeolite |
|---|---|---|---|---|
| III | 1.7 | 5.3 | 30 | X & A |
| IV | 1.0 | 7 | 30 | X |
| V | 1.8 | 7 | 30 | A |
| VI | 0.7 | 9.8 | 15.8 | X & A |
| VII | 0.56 | 7.8 | 20 | Y |

Thus, in operation, either zeolite X, zeolite A or a combination of the two or zeolite Y can be formed by dissolving sand in a sodium hydroxide solution to form a sodium silicate solution, forming a sodium aluminate solution, quickly adding the sodium aluminate solution to the sodium silicate solution to form a mixture having a certain composition, reacting the mixture at a temperature of from 80° to 120° C. until a zeolite is formed, then recovering the zeolite. The type of zeolite formed depends on the composition of the reaction mixture.

While the present invention has been described with reference to specific embodiments, this application is intended to cover those various changes and substitutions which may be made by those skilled in the art without departing from the spirit and scope of the appended claims.

I claim:

1. A method of producing zeolite A comprising the steps of:
   (a) forming a sodium aluminate solution;
   (b) forming a sodium silicate solution by:
      (i) dissolving sand in a sodium hydroxide solution at a pressure of at least 200 psig heated to a temperature of at least 130° C. to produce a sodium silicate solution having a silica to sodium oxide molar ratio of between 2.4:1 and 2.8:1;
      (ii) activating said sodium silicate solution with from 50 to 2000 ppm alumina at a temperature of between 15° and 100° C. for at least 10 minutes; and
      (iii) heating said sodium silicate solution to between 80° and 120° C.;
   (c) adding said sodium aluminate solution to said sodium silicate solution to produce a reaction mixture comprising a sodium silicate mother liquor and an amorphous sodium alumino silicate pigment, in total having a sodium oxide to silica molar ratio of between 1:1 and 2.5:1; a silica to alumina molar ratio of between 3:1 and 10:1; and a water to sodium oxide molar ratio of between 10:1 and 35:1;
   (d) heating said mixture to a temperature of from 80° to 120° C.;
   (e) reacting said mixture at a temperature of from 80° to 120° C. until zeolite A is formed; and
   (f) recovering said zeolite A.

2. A method according to claim 1 wherein the amount of alumina used to activate said sodium silicate is from 400 to 600 ppm and said activation occurs at room temperature.

3. A method according to claim 1 wherein the amount of alumina used to activate said sodium silicate is about 600 ppm and said activation occurs at room temperature.

4. A method according to claim 1 wherein the mixture has a sodium oxide to silica molar ratio of between 1.4:1 and 2:1; a silica to alumina molar ratio of between 3:1 and 7:1; and a water to sodium oxide molar ratio of between 25:1 and 35:1.

5. A method of producing a pure crystalline zeolite A comprising:
- (a) dissolving sand in a sodium hydroxide solution at a pressure of about 140 psig and a temperature of at least 130° C. to produce a sodium silicate solution having a silica to sodium oxide molar ratio of about 2.4:1;
- (b) activating said sodium silicate solution with about 600 ppm alumina at room temperature for at least 10 minutes;
- (c) heating said sodium silicate solution to a temperature of about 90° C.;
- (d) forming a sodium silicate solution;
- (e) heating said sodium aluminate solution to a temperature of about 90° C.;
- (f) adding a sodium aluminate solution to said sodium silicate solution so that all of the sodium aluminate solution is added within a period of time less than 30 seconds to form a mixture having a sodium oxide to silica molar ratio of about 1.8:1; a silica to alumina molar ratio of about 7:1; and a water to sodium oxide molar ratio of about 30:1;
- (g) heating said mixture to a temperature of about 100° C.;
- (h) reacting said mixture at a temperature of about 100° C. until crystalline zeolite A is formed; and
- (i) recovering said zeolite A.

* * * * *

UNITED STATES PATENT AND TRADEMARK OFFICE
CERTIFICATE OF CORRECTION

PATENT NO. : 4,235,856
DATED : November 25, 1980
INVENTOR(S) : John A. Kostinko

It is certified that error appears in the above—identified patent and that said Letters Patent is hereby corrected as shown below:

Column 1, line 22, "ahe" should be -- the --.

Column 3, line 21, "Tabble" should be -- Table --.

Column 4, between lines 10-15, in columnar heading, "A" should be -- $\overset{\circ}{A}$ --.

Column 6, line 6, in third column, "1.78-176" should be -- 1.78-1.76 --.

Column 6, line 67, preceding the word "pressures", the word -- partial -- should be inserted.

Column 9, line 5, "c stability" should be -- hydrolytic stability --.

Column 9, line 8, "zeolite" (second instance) should be -- zeolite X --.

Column 10, line 41, "hydrate" should be -- hydrated --.

Column 11, line 13, at first of line, delete "$SiO_2/Al_2O_3$ ratio of 1:1 and a".

Column 11, line 15, following "5:1" insert a period -- . --.

Column 12, line 9, "fully" should be -- fuller --.

Column 21, line 10, "Sodiium" should be -- Sodium --.

Column 21, line 24, "oxide ratios" should be -- oxide mole ratios --.

Column 21, line 53, "time" (first instance) should be -- mixture --.

UNITED STATES PATENT AND TRADEMARK OFFICE
CERTIFICATE OF CORRECTION

PATENT NO. : 4,235,856
DATED : November 25, 1980
INVENTOR(S) : John A. Kostinko

It is certified that error appears in the above—identified patent and that said Letters Patent is hereby corrected as shown below:

Column 25, line 15, "sodium silicate" should be -- sodium aluminate --.

Signed and Sealed this

Twenty-first Day of April 1981

[SEAL]

Attest:

RENE D. TEGTMEYER

*Attesting Officer*     *Acting Commissioner of Patents and Trademarks*